(12) United States Patent
Okamoto

(10) Patent No.: US 9,839,645 B2
(45) Date of Patent: Dec. 12, 2017

(54) AGENTS FOR KILLING HIV-1-INFECTED CELLS AND APPLICATION THEREOF

(71) Applicant: KAGOSHIMA UNIVERSITY, Kagoshima-shi, Kagoshima (JP)

(72) Inventor: Mika Okamoto, Kagoshima (JP)

(73) Assignee: KAGOSHIMA UNIVERSITY, Kogoshima-Shi, Kagoshima (JP)

( * ) Notice: Subject to any disclaimer, the term of this patent is extended or adjusted under 35 U.S.C. 154(b) by 0 days.

(21) Appl. No.: 15/651,667

(22) Filed: Jul. 17, 2017

(65) Prior Publication Data

US 2017/0312296 A1 Nov. 2, 2017

Related U.S. Application Data

(63) Continuation-in-part of application No. PCT/JP2016/051768, filed on Jan. 22, 2016.

(30) Foreign Application Priority Data

Jan. 23, 2015 (JP) .................. 2015-011506
Jun. 12, 2015 (JP) .................. 2015-119111

(51) Int. Cl.
| | | |
|---|---|---|
| A61K 31/41 | (2006.01) | |
| A61K 31/165 | (2006.01) | |
| A61K 31/135 | (2006.01) | |
| A61K 31/675 | (2006.01) | |
| A61K 31/4406 | (2006.01) | |
| A61K 31/167 | (2006.01) | |
| A61K 31/472 | (2006.01) | |
| A61K 31/34 | (2006.01) | |

(52) U.S. Cl.
CPC .......... *A61K 31/675* (2013.01); *A61K 31/167* (2013.01); *A61K 31/34* (2013.01); *A61K 31/4406* (2013.01); *A61K 31/472* (2013.01)

(58) Field of Classification Search
CPC ... C07D 213/40; A61K 31/165; A61K 31/135
USPC ........................................ 514/357, 620, 649
See application file for complete search history.

(56) References Cited

U.S. PATENT DOCUMENTS

| | | | |
|---|---|---|---|
| 6,174,905 B1 | 1/2001 | Suzuki et al. | |
| 7,244,751 B2 | 7/2007 | Lu et al. | |
| 2010/0324034 A1 | 12/2010 | Hazuda et al. | |

FOREIGN PATENT DOCUMENTS

| | | |
|---|---|---|
| CN | 1040169106 A | 10/2014 |
| JP | 10-152462 A | 6/1998 |
| JP | 2007527362 A | 9/2007 |
| WO | 2008097654 A1 | 8/2008 |
| WO | 2014189648 A1 | 11/2014 |

OTHER PUBLICATIONS

Ricky W. Johnstone, "Histone-Deacetylase Inhibitors: Novel Drugs for the Treatment of Cancer," Nature Reviews Drug Discovery, Apr. 1, 2002, vol. 1, pp. 287-299.

Qing-Wei Zhang et al., "Synthesis and Biological Evaluation of N-(Aminopyridine) Benzamide Analogues as Histone Deacetylase Inhibitors," Bull. Korean Chem. Soc., 2012, vol. 33, No. 2, pp. 535-540.

Steven G. Deeks, "Shock and kill," Nature, Jul. 26, 2012, vol. 487 (7408), pp. 439-440.

Fiona Wightman et al., "Entinostat is a histone deacetylase inhibitor selective for class 1 histone deacetylases and activates HIV production from latently infected primary T cells," AIDS, 2013, vol. 27, No. 18, pp. 2853-2862.

English translation of PCT International Search Report issued in connection with PCT international application No. PCT/JP2016/051768, filed Jan. 22, 2016, dated Apr. 26, 2016 (2 pages).

*Primary Examiner* — Raymond J Henley, III
(74) *Attorney, Agent, or Firm* — Lucas & Mercanti, LLP

(57) ABSTRACT

The present invention relates to an agent for killing HIV-1-infected cells, comprising a compound represented by formula (I):

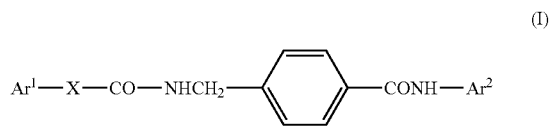

wherein $Ar^1$ and $Ar^2$ are the same or different and represent a substituted or unsubstituted aromatic group, and X represents —$CH_2O$— or —CH=CH—, its salt, or their solvate, and a combined preparation for simultaneous, separate, or sequential administration in treating or preventing HIV-1 infection, comprising two separate preparations: (a) a preparation comprising a compound represented by the formula (I), its salt, or their solvate, and (b) a preparation comprising an anti-HIV-1 drug.

6 Claims, 17 Drawing Sheets

Fig. 5 Experimental procedure (Example 3)

Fig. 8 Experimental procedure (Example 4)

Fig. 10 Experimental procedure (Example 5)

Fig. 13 Experimental procedure (Example 6)

Fig. 15 Experimental procedure (Example 6)

AGENTS FOR KILLING HIV-1-INFECTED CELLS AND APPLICATION THEREOF

CROSS-REFERENCE TO RELATED APPLICATIONS

This application is a Continuation-in-part of PCT/JP2016/051768, filed Jan. 22, 2016, which claims the benefit of Japanese Patent Application No. 2015-011506, filed Jan. 23, 2015 and No. 2015-119111, filed Jun. 12, 2015, the contents of each of which are incorporated herein by reference.

TECHNICAL FIELD

The present invention relates to an agent used for treating HIV-1 infection.

BACKGROUND ART

In the whole world in 2013, the number of HIV-1-infected people was about 35 million and the number of newly HIV-1-infected people was about 2.1 million; HIV-1 infection is still globally a major public health problem.

However, current anti-HIV-1 drugs can suppress HIV-1 proliferation but cannot eliminate HIV-1-infected cells from the body of infected people. Hence, HIV-1-infected people must take anti-HIV-1 drugs over a lifetime, posing problems of the chronic toxicity due to the long-term use of these anti-HIV-1 drugs and the appearance of drug-resistant HIV-1. Thus, there is now an increased need for the development of a radical treatment for HIV-1 infection. The medical cost per person with HIV-1 infection is said to be about 1 million dollars when the treatment period is assumed to be about 40 years, and such high medical cost becomes a socially major problem; there is a world-wide need for the development of a radical treatment for HIV-1.

The main cause for the fact that the complete cure of HIV-1 infection is difficult is the presence of HIV-1 latently infected cells. The latently infected cells are mainly HIV-1-infected cells derived from resting memory $CD4^+$ T cells having a long life length; HIV-1 is present as proviral DNA in genomic DNA in these cells, and HIV-1 particles or HIV-1 proteins are little produced in a state free of cell activating stimulus, such as a proliferative stimulus; however, the activating stimuli are given to start HIV-1 production. Most of current anti-HIV-1 drugs can suppress HIV-1 production since they target HIV-1-derived enzymes, but cannot decrease the number of HIV-1 latently infected cells. Thus, to establish a radical treatment of HIV-1, the development of a treatment method targeting HIV-1 latently infected cells is needed.

A histone deacetylase (HDAC) inhibitor, affecting gene expression by suppressing the action of histone deacetylase to cause the hyperacetylation of histone, exerts an antitumor effect by changing the expression of an oncogene or a tumor suppressor. Some HDAC inhibitors are each already in the early stage of clinical development as a monotherapy or a combination therapy as a method for treating solid and hematological tumors.

There is known to be a relationship between chronic infection and carcinogenesis, e.g., hepatitis C virus infection and liver cell carcinoma, and *Helicobacter pylori* infection and stomach cancer. This is considered to involve that chronic inflammation has molecular mechanisms in common with cancer, such as the activation of an inflammatory signaling system and the induction of expression of various genes.

It has recently been reported that some HDAC inhibitors, such as entinostat and vorinostat activate HIV-1 latently infected cells (reservoir cells) to induce HIV-1 production. (Ricky W. Johnstone, Nature Reviews Drug Discovery 1, 287-299 (1 Apr. 2002))

JP Patent Publication (Kokai) No. 10-152462 A and JP Patent Publication (Kohyo) No. 2007-527362 A and Qing-Wei Zhang and Jian-Qi Li, Bull. Korean Chem. Soc. 2012, Vol. 33, No. 2 535 (http://dx.doi.org/10.5012/bkcs.2012.33.2.535) state that benzamide derivatives, such as entinostat and chidamide, as HDAC inhibitors are useful as therapeutic and improving agents for malignant tumor, autoimmune disease, dermatologic disease, and parasitic infection.

There has not previously been any report of the specific cell death-inducing effect of entinostat on HIV-1-infected human mononuclear cells.

SUMMARY OF INVENTION

Technical Problem

An object of the present invention is to provide an agent capable of specifically inducing cell death in HIV-1 latently infected cells.

Solution to Problem

The present inventors have conceived that an HDAC inhibitor has the possibility of specifically inducing cell death in HIV-1 latently infected cells as chronically infected cells.

Accordingly, as a result of preparing an HIV-1 chronically infected cell model derived from human peripheral blood mononuclear cells in vitro and exposing the model to entinostat, cell death has been specifically and selectively induced in the HIV-1-infected human peripheral blood mononuclear cells.

However, entinostat activates HIV-1 production in infected cells and has the possibility of causing secondary infection. As such, the use of entinostat alone results in the new production of HIV-1-infected cells. Accordingly, as a result of performing a combination experiment with a protease inhibitor acting on the later process of HIV-1 replication to suppress the replication of HIV-1, both nelfinavir (NFV) and saquinavir (SQV) as HIV-1 protease inhibitors have concentration-dependently suppressed HIV-1 production in the presence of entinostat; however, these protease inhibitors have not affected the cell death-inducing effect specific for HIV-1-infected cells due to entinostat. From these results, it has been probable that the combined use of entinostat and an anti-HIV-1 drug, such as an HIV-1 protease inhibitor, has the possibility of completely curing HIV-1 infection by decreasing the number of HIV-1-infected cells while suppressing secondary infection due to HIV-1 production activated by entinostat.

Thus, the subject matter of the present invention is as follows.

(1) An agent for killing HIV-1-infected cells, comprising a compound represented by formula (I):

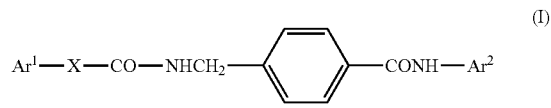

where $Ar^1$ and $Ar^2$ are the same or different and represent a substituted or unsubstituted aromatic group, and X represents —CH₂O— or —CH═CH—, a salt thereof, or a solvate of these.

(2) The agent for killing HIV-1-infected cells according to (1) above, wherein in the formula (I), $Ar^1$ and $Ar^2$ are the same or different and represent a phenyl group or a pyridyl group, and the phenyl group or the pyridyl group is optionally substituted by one or more substituents selected from an amino group, $C_1$ to $C_6$ alkyl groups, and halogen atoms.

(3) The agent for killing HIV-1-infected cells according to (1) above, wherein in the formula (I), $Ar^1$ represents a pyridyl group and $Ar^2$ represents a phenyl group optionally substituted by one or more substituents selected from an amino group and halogen atoms.

(4) The agent for killing HIV-1-infected cells according to any of (1) to (3) above, wherein the agent is to be administered to an HIV-1-infected person not suffering from cancer.

(5) A composition for treating or preventing HIV-1 infection, comprising a compound represented by the formula (I) according to (1) above, a salt thereof, or a solvate of these, and an anti-HIV-1 drug.

(6) The composition for treating or preventing HIV-1 infection according to (5) above, wherein the anti-HIV-1 drug is at least one selected from HIV-1 protease inhibitors.

(7) A combined preparation for simultaneous, separate, or sequential administration in treating or preventing HIV-1 infection, comprising two separate preparations:
(a) a preparation comprising a compound represented by the formula (I) according to (1) above, a salt thereof, or a solvate of these, and
(b) a preparation comprising an anti-HIV-1 drug.

(8) The combined preparation according to (7) above, wherein the anti-HIV-1 drug is at least one selected from HIV-1 protease inhibitors.

Advantageous Effects of Invention

In accordance with the agent for killing HIV-1-infected cells according to the present invention, cell death can be specifically induced in HIV-1 latently infected cells. The combined use of the agent for killing HIV-1-infected cells according to the present invention and an anti-HIV-1 drug, such as an HIV-1 protease inhibitor, can completely cure HIV-1 infection by decreasing the number of HIV-1-infected cells while suppressing secondary infection due to HIV production activation by a compound represented by the formula (I).

DESCRIPTION OF EMBODIMENTS

Figure 1:
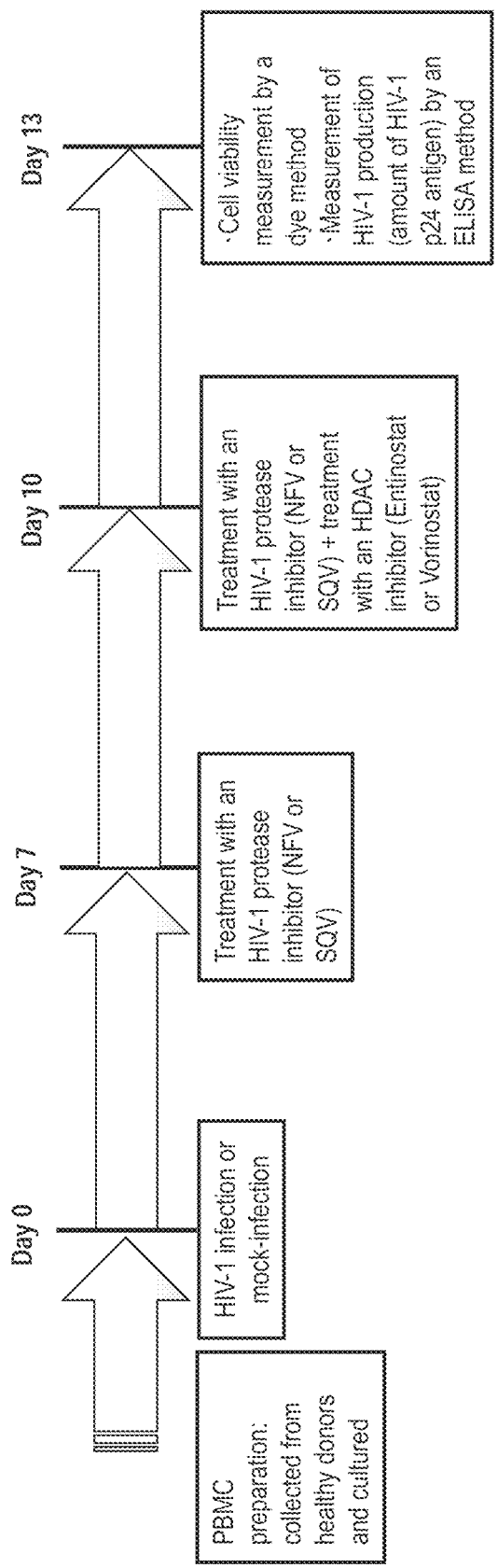
FIG. 1 is a diagram showing the experimental procedure adopted in Example 2.

The present invention will be described below in detail.
Examples of the aromatic group represented by $Ar^1$ or $Ar^2$ in the formula (I) include aromatic hydrocarbon groups, such as a phenyl group, a tolyl group, and a naphthyl group; and aromatic heterocycle groups, such as a furyl group, a thienyl group, a pyrrolyl group, an oxazolyl group, an isooxazolyl group, a thiazolyl group, an isothiazolyl group, an imidazolyl group, a pyrazolyl group, a pyridyl group, a pyrimidinyl group, a pyridazinyl group, a pyrazinyl group, a quinolyl group, and an isoquinolyl group.

Examples of the substituent in an aromatic group represented by $Ar^1$ or $Ar^2$ in the formula (I) include $C_1$ to $C_6$ alkyl groups, such as a methyl group, an ethyl group, a propyl group, an isopropyl group, a butyl group, an isobutyl group, a sec-butyl group, a tert-butyl group, a pentyl group, an isopentyl group, a hexyl group, a cyclopropyl group, a cyclobutyl group, a cyclopentyl group, and a cyclohexyl group; $C_1$ to $C_6$ alkoxy groups, such as a methoxy group, an ethoxy group, a propoxy group, an isopropoxy group, a butoxy group, an isobutoxy group, a sec-butoxy group, a tert-butoxy group, a pentyloxy group, an isopentyloxy group, a hexyloxy group, a cyclopropyloxy group, a cyclobutyloxy group, a cyclopentyloxy group, and a cyclohexyloxy group; $C_1$ to $C_6$-alkoxy-carbonyl groups, such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxycarbonyl group, a cyclopropyloxycarbonyl group, a cyclobutyloxycarbonyl group, and a cyclopentyloxycarbonyl group; a hydroxyl group; aromatic hydrocarbon groups, such as a phenyl group, a tolyl group, and a naphthyl group; halogen atoms, such as a fluorine atom, a chlorine atom, a bromine atom, and an iodine atom; aralkyl groups, such as a benzyl group and a phenethyl group; $C_1$ to $C_6$-aliphatic acyl groups, such as a formyl group, an acetyl group, a propionyl group (a propanoyl group), a butylyl group (a butanoyl group), a valeryl group (a pentanoyl group), and a hexanoyl group; aromatic acyl groups (aroyl groups), such as a benzoyl group and a toluoyl group; aralkyloxy groups, a carboxyl group, an amino group, $C_1$ to $C_6$-alkylamino groups, and di-$C_1$ to $C_6$-alkylamino groups.

The aromatic group represented by $Ar^1$ or $Ar^2$ is preferably a substituted or unsubstituted phenyl or a pyridyl (2-pyridyl, 3-pyridyl, or 4-pyridyl) group.

Examples of the substituted phenyl group include, but not limited to, a 4-aminophenyl group, a 3-aminophenyl group, a 2-aminophenyl group, a 2-amino-4-fluorophenyl group, a 2-amino-4-chlorophenyl group, a 2-amino 5-fluorophenyl group, a 2-amino-5-chlorophenyl group, a 4-methylphenyl group (a p-tolyl group), a 3-methylphenyl group (a m-tolyl group), a 2-methylphenyl group (an o-tolyl group), a 4-ethylphenyl group, a 3-ethylphenyl group, a 2-ethylphenyl group, a 4-n-propylphenyl group, a 4-isopropylphenyl group, a 2-isopropylphenyl group, a 4-n-butylphenyl group, a 4-isobutylphenyl group, a 4-sec-butylphenyl group, a 2-sec-butylphenyl group, a 4-tert-butylphenyl group, a 3-tert-butylphenyl group, a 2-tert-butylphenyl group, a 4-n-pentylphenyl group, a 4-isopentylphenyl group, a 2-neopentylphenyl group, a 4-tert-pentylphenyl group, a 4-n-hexylphenyl group, a 4-(2-ethylbutyl)phenyl group, a 4-n-heptylphenyl group, a 4-n-octylphenyl group, a 4-(2-ethylhexyl)phenyl group, a 4-tert-octylphenyl group, a 4-n-decylphenyl group, a 4-n-dodecylphenyl group, a 4-n-tetradecylphenyl group, a 4-cyclopentylphenyl group, a 4-cyclohexylphenyl group, a 4-(4-methylcyclohexyl)phenyl group, a 4-(4-tert-butylcyclohexyl)phenyl group, a 3-cyclohexylphenyl group, a 2-cyclohexylphenyl group, a 2,4-dimethylphenyl group, a 2,5-dimethylphenyl group, a 3,4-dimethylphenyl group, a 3,5-dimethylphenyl group, a 2,6-dimethylphenyl group, a 2,4-diethylphenyl group, a 2,3,5-trimethylphenyl group, a 2,3,6-trimethylphenyl group, a 3,4,5-trimethylphenyl group, a 2,6-diethylphenyl group, a 2,5-diisopropylphenyl group, a 2,6-diisobutylphenyl group, a 2,4-di-tert-butylphenyl group, a 2,5-di-tert-butylphenyl group, a 4,6-di-tert-butyl-2-methylphenyl group, a 5-tert-butyl-2-methylphenyl group, a 4-tert-butyl-2,6-dimethylphenyl group, a 4-methoxyphenyl group, a 3-methoxyphenyl group, a 2-methoxyphenyl group, a 4-ethoxyphenyl group, a 3-ethoxyphenyl group, a 2-ethoxyphenyl group, a 4-n-propoxyphenyl group, a 3-n-propoxyphenyl group, a 4-isopropoxyphenyl group, a 2-isopropoxyphenyl group, a 4-n-butoxyphenyl group, a 4-isobutoxyphenyl group, a 2-sec-butoxyphenyl group, a 4-n-pentyloxyphenyl group, a 4-isopentyloxyphenyl group, a 2-isopentyloxyphenyl group, a 4-neopentyloxyphenyl group, a 2-neopentyloxyphenyl group, a 4-n-hexyloxyphenyl group, a 2-(2-ethylbutyl)oxyphenyl group, a 4-n-octyloxyphenyl group, a 4-n-decyloxyphenyl group, a 4-n-dodecyloxyphenyl group, a 4-n-tetradecyloxyphenyl group, a 4-cyclohexyloxyphenyl group, a 2-cyclohexyloxyphenyl group, a 2-methyl-4-methoxyphenyl group, a 2-methyl-5-methoxyphenyl group, a 3-methyl-4-methoxyphenyl group, a 3-methyl-5-methoxyphenyl group, a 3-ethyl-5-methoxyphenyl group, a 2-methoxy-4-methylphenyl group, a 3-methoxy-4-methylphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, a 3,5-diethoxyphenyl group, a 3,5-di-n-butoxyphenyl group, a 2-methoxy-4-ethoxyphenyl group, 2-methoxy-6-ethoxyphenyl group, a 3,4,5-trimethoxyphenyl group, a 4-hydroxyphenyl group, a 3-hydroxyphenyl group, a 2-hydroxyphenyl group, a 4-methoxycarbonylphenyl group, a 3-methoxycarbonylphenyl group, a 2-methoxycarbonylphenyl group, a 4-biphenylyl group, a 3-biphenylyl group, a 2-biphenylyl group, a 4-(4-methylphenyl)phenyl group, a 4-(3-methylphenyl)phenyl group, a 4-(4-methoxyphenyl)phenyl group, a 4-(4-n-butoxyphenyl)phenyl group, a 2-(2-methoxyphenyl)phenyl group, a 4-(4-chlorophenyl)phenyl group, a 3-methyl-4-phenylphenyl group, a 3-methoxy-4-phenylphenyl group, terphenyl group, a 3,5-diphenylphenyl group, a 4-fluorophenyl group, a 3-fluorophenyl group, a 2-fluorophenyl group, a 4-chlorophenyl group, a 3-chlorophenyl group, a 2-chlorophenyl group, a 4-bromophenyl group, a 2-bromophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3-dichlorophenyl group, a 2,4-dichlorophenyl group, a 2,5-dichlorophenyl group, a 3,4-dichlorophenyl group, a 3,5-dichlorophenyl group, a 2,5-dibromophenyl group, a 2,4,6-trichlorophenyl group, a 2-fluoro-4-methylphenyl group, a 2-fluoro-5-methylphenyl group, a 3-fluoro-2-methylphenyl group, a 3-fluoro-4-methylphenyl group, a 2-methyl-4-fluorophenyl group, a 2-methyl-5-fluorophenyl group, a 3-methyl-4-fluorophenyl group, a 2-chloro-4-methylphenyl group, a 2-chloro-5-methylphenyl group, a 2-chloro-6-methylphenyl group, a 2-methyl-3-chlorophenyl group, a 2-methyl-4-chlorophenyl group, a 3-chloro-4-methylphenyl group, a 3-methyl-4-chlorophenyl group, a 2-chloro-4,6-dimethylphenyl group, a 2-methoxy-4-fluorophenyl group, a 2-fluoro-4-methoxyphenyl group, a 2-fluoro-4-ethoxyphenyl group, a 2-fluoro-6-methoxyphenyl group, a 3-fluoro-4-ethoxyphenyl group, a 3-chloro-4-methoxyphenyl group, a 2-methoxy-5-chlorophenyl group, a 3-methoxy-6-chlorophenyl group, and a 5-chloro-2,4-dimethoxyphenyl group.

Examples of the substituted pyridyl group include, but not limited to, a 3-chloro-2-pyridyl group, a 4-chloro-2-pyridyl group, a 5-chloro-2-pyridyl group, a 6-chloro-2-pyridyl group, a 3-methyl-2-pyridyl group, a 4-methyl-2-pyridyl group, a 5-methyl-2-pyridyl group, a 6-methyl-2-pyridyl group, a 2-amino-3-pyridyl group, a 2-amino-6-chloro-3-pyridyl group, a 2-amino-6-fluoro-3-pyridyl group, a 2-amino-5-chloro-3-pyridyl group, and a 2-amino-5-fluoro-3-pyridyl group.

The aromatic group represented by $Ar^1$ is preferably a substituted or unsubstituted nitrogen-containing aromatic heterocycle group (for example, a pyrrolyl group, an oxazolyl group, an isooxazolyl group, a thiazolyl group, an isothiazolyl group, an imidazolyl group, a pyrazolyl group, a pyridyl group, a pyrimidinyl group, a pyridazinyl group, a pyrazinyl group, a quinolyl group, or an isoquinolyl group), more preferably a substituted or unsubstituted pyridyl group, particularly a substituted or unsubstituted 3-pyridyl group.

The aromatic group represented by $Ar^2$ is preferably a phenyl or pyridyl group substituted by at least an amino group, more preferably a phenyl group substituted at least at the 2-position by an amino group (for example, a 2-amino-4-fluorophenyl group or a 2-amino-4-chlorophenyl group), a 2-amino-3-pyridyl group, a 2-amino-6-chloro-3-pyridyl group, or a 2-amino-6-fluoro-3-pyridyl group.

When the compound represented by the formula (I) has a basic substituent, such as an amino group or a pyridyl group, or an acidic substituent, such as a phenolic hydroxyl group or a carboxyl group, it can also be used in the form of a salt, preferably a pharmaceutically acceptable salt, for example, a salt with an inorganic acid, such as hydrochloric acid, sulfuric acid, phosphoric acid, hydrobromic acid, hydroiodic acid, nitric acid, pyrosulfuric acid, or metaphosphoric acid, or an organic acid, such as citric acid, benzoic acid, acetic acid, propionic acid, fumaric acid, maleic acid, sulfonic acid (e.g., methanesulfonic acid, p-toluenesulfonic acid, or naphthalenesulfonic acid); or an alkali metal salt, such as a sodium salt or a potassium salt.

Examples of the solvate of a compound represented by the formula (I) include hydrates.

Among compounds represented by the formula (I), a compound (Ia) in which X is —CH$_2$O— in the formula (I) can be produced in the way described below according to a well-known method, for example, the method described in JP Patent Publication (Kokai) No. 10-152462 A.

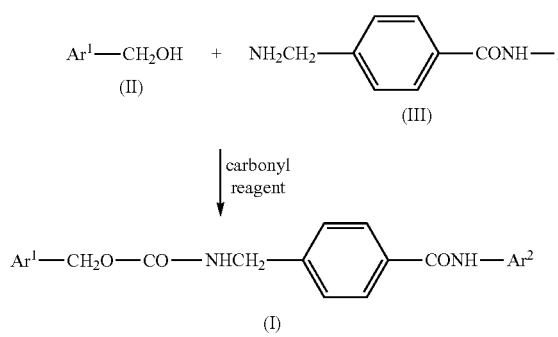

wherein Ar$^1$ and Ar$^2$ have the same meanings as those described above.

Thus, a compound represented by the formula (II) and a compound represented by the formula (III) can be subjected to condensation reaction using a carbonyl reagent, such as N, N'-carbonyldiimidazole or phosgene, to provide a compound represented by the formula (I).

Examples of the solvate of a compound represented by the formula (I) include hydrates.

Among compounds represented by the formula (I), a compound (Ib) in which X is —CH═CH— in the formula (I) can be produced in the way described below according to a well-known method, for example, the method described in JP Patent Publication (Kohyo) No. 2007-527362 A.

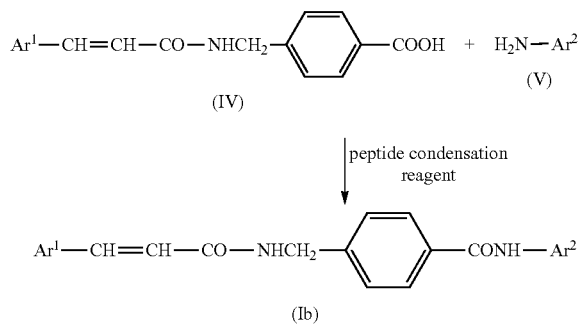

wherein Ar$^1$ and Ar$^2$ have the same meanings as those described above.

(1) Thus, a compound represented by the formula (IV) and a compound represented by the formula (V) can be subjected to condensation reaction using a peptide condensation reagent, such as dicyclohexylcarbodiimide, N, N'-carbonyldiimidazole, diphenylphosphoryl azide, or diethylphosphoryl cyanide, to provide a compound represented by the formula (Ib).

When the aromatic group represented by Ar$^1$ or Ar$^2$ in the formulas (Ia) and (Ib) is substituted by an amino group, it is protected with a protecting group used for a typical peptide formation reaction, such as a tert-butoxycarbonyl group, and deprotected after reaction. When the aromatic group represented by Ar$^1$ or Ar$^2$ is substituted by a hydroxyl group, it is protected with a protecting group used for a typical peptide formation reaction, such as a benzyl group, and deprotected after reaction.

Some of compounds represented by the formula (I), such as entinostat represented by the following formula (1):

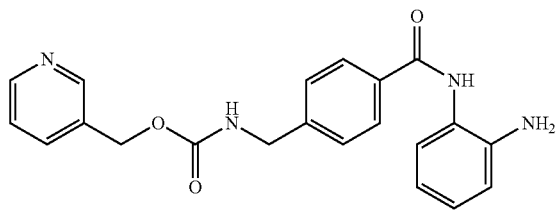 [SMILES: Nc1ccccc1NC(=O)c1ccc(CNC(=O)OCc2cccnc2)cc1]

and chidamide represented by the following formula (2):

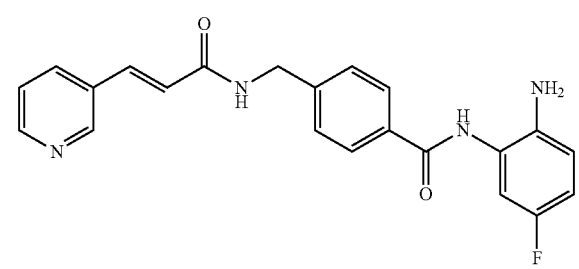 [SMILES: Nc1ccc(F)cc1NC(=O)c1ccc(CNC(=O)/C=C/c2cccnc2)cc1]

are commercially available and these marketed products can be used.

In order to purify the product obtained as described above, any usually employed method, such as column chromatography using silica gel or the like as a carrier, or a recrystallization method using methanol, ethanol, chloroform, dimethyl sulfoxide, n-hexane-ethyl acetate, water or the like, may be employed. Examples of an eluent used in the column chromatography include methanol, ethanol, chloroform, acetone, hexane, dichloromethane, ethyl acetate and a mixed solvent of any of them.

The compound represented by the formula (I) can be formulated as an agent for killing HIV-1-infected cells in combination with a commonly used pharmaceutical carrier. The administration form is not especially limited but appropriately selected for use depending upon the situation, and examples include oral agents such as a tablet, a capsule, granules, fine granules, a powder, a controlled release preparation, a solution, a suspension, an emulsion, a syrup and an elixir, and parenteral agents such as an injection and a suppository.

An oral agent is produced by a general method using, for example, starch, lactose, sucrose, mannite, carboxymethyl cellulose, a mineral salt or the like. In addition, a binder, a disintegrator, a surface active agent, a lubricant, a fluidity improver, a corrigent, a coloring agent, a flavor and the like can be appropriately added.

Examples of the binder include starch, dextrin, acacia, gelatin, hydroxypropyl starch, methyl cellulose, carboxymethyl cellulose sodium, hydroxypropyl cellulose, crystalline cellulose, ethyl cellulose, polyvinyl pyrrolidone and macrogol.

Examples of the disintegrator include starch, hydroxypropyl starch, carboxymethyl cellulose sodium, carboxymethyl cellulose calcium, carboxymethyl cellulose and low substituted hydroxypropyl cellulose.

Examples of the surface active agent include sodium lauryl sulfate, soybean lecithin, sucrose fatty acid ester and polysorbate 80.

Examples of the lubricant include talc, waxes, hydrogenated vegetable oil, sucrose fatty acid ester, magnesium stearate, calcium stearate, aluminum stearate and polyethylene glycol.

Examples of the fluidity improver include light anhydrous silicic acid, dried aluminum hydroxide gel, synthetic aluminum silicate and magnesium silicate.

An injection is produced by a general method, and as a diluent, distilled water for injection, physiological saline, an aqueous glucose solution, olive oil, sesame oil, peanut oil, soybean oil, corn oil, propylene glycol, polyethylene glycol or the like can be generally used. Furthermore, a bactericide, an antiseptic agent, a stabilizer, a tonicity adjusting agent, a soothing agent or the like may be added if necessary. Furthermore, from the viewpoint of stability, an injection filled in a vial or the like may be frozen for removing moisture by a general freeze-drying technique, so that a solution can be re-prepared from the freeze-dried product immediately before use. A ratio of the compound represented by the formula (I) in an injection can be varied in a range of 5 to 50% by weight, but the ratio is not limited to this range.

Other examples of the parenteral agent include a suppository or the like for endorectal administration, which is produced by a general method.

An agent for killing HIV-1-infected cells thus formulated can be administered, for example, at 1 to 4 doses per day for 1 week to 3 months depending upon the formulation, the route of administration, etc.

In order to show a desired effect as an oral agent, it is appropriate to administer to, for example, an adult patient generally in an amount of 0.1 to 1000 mg and preferably 1 to 500 mg, in terms of the weight of the compound represented by the formula (I), in one or several doses per day, although the amount is varied depending upon the age, the weight and the degree of disease of the patient.

In order to show a desired effect as a parenteral agent, it is appropriate to administer to, for example, an adult patient generally in an amount of 0.1 to 1000 mg and preferably 1 to 500 mg, in terms of the weight of the compound represented by the formula (I), by intravenous injection, intravenous drip, hypodermic injection or intramuscular injection, although the amount is varied depending upon the age, the weight and the degree of disease of the patient.

Furthermore, the compound represented by the formula (I) may be used in combination with another drug effective against HIV-1 infection. Such a drug can be separately administered during the process of the treatment, or can be combined with the compound represented by the formula (I) in a single formulation of, for example, a tablet, an intravenous solution or a capsule.

A compound of the formula (I) activates HIV-1 production in infected cells and has the possibility of causing secondary infection. As such, the use of a compound of the formula (I) alone results in the new production of HIV-1-infected cells.

Accordingly, its combined use with an HIV-1 protease inhibitor having a different action site from that of an HDAC inhibitor and acting on the later process of HIV-1 replication to suppress HIV-1 replication, can completely cure HIV-1 infection by decreasing the number of HIV-1-infected cells while suppressing secondary infection due to HIV-1 production activation by a compound of the formula (I).

Examples of the HIV-1 protease inhibitor include, but not limited to, commercial HIV-1 protease inhibitors, such as nelfinavir, saquinavir, atazanavir, lopinavir, ritonavir, indinavir, darunavir, amprenavir, fosamprenavir, and tipranavir, and derivatives and alalogs of any of these compounds.

Preferred examples of the preferred combination of an HDAC inhibitor and an HIV-1 protease inhibitor include a combination of darunavir and entinostat.

In one embodiment, the HIV-1 protease inhibitor is administered at a total daily dose of 200 mg to 2,500 mg to a subject. In a preferred embodiment, the HIV-1 protease inhibitor is administered at a total daily dose of 500 mg to 2,250 mg to a subject. In the most preferred embodiment, the HIV-1 protease inhibitor is administered at a total daily dose of 750 mg to 2,250 mg, or 750 mg or about 750 mg, or 1,250 mg or about 1,250 mg, or 1,500 mg or about 1,500 mg, or 2,250 mg or about 2,250 mg to a subject.

The compound of the formula (I) has the effect of selectively killing HIV-1-infected peripheral lymphocytes during a period of chronic infection.

Thus, the pharmaceutical composition of the present invention is preferably administered during the chronic infection period of HIV-1 infection. The chronic infection period is characterized by a plurality of antibodies against HIV-1 and a limited Th1/CTL response.

The present specification encompasses the contents of the specifications of Japanese Patent Application Nos. 2015-11506 and 2015-119111 on which the priority of the present application is based.

EXAMPLES

The present invention will be described below in detail based on Examples. However, the present invention is not intended to be limited thereto.

In the following Examples, entinostat was used as a compound represented by the formula (I) since it was marketed and easily available.

Example 1 Cell Death-Inducing Effect Specific for HIV-1-Infected Cell (Human Peripheral Blood Mononuclear Cell)

Healthy person-derived peripheral blood mononuclear cells were infected with HIV-1 strain III$_B$ in vitro to prepare an HIV-1 chronically infected cell model derived from human peripheral blood mononuclear cells, which was then exposed to entinostat as an HDAC inhibitor.

During the HIV-1 later infection period, entinostat of 0.25 to 0.5 µM specifically and selectively induced cell death in HIV-1-infected human peripheral blood mononuclear cells. The concentration of 0.5 µM decreased the cell viability of HIV-1-infected cells to about 50% of the cell viability of pseudo-infected (non-infected) cells.

Example 2 Combination Effect of HIV-1 Protease Inhibitor and HDAC Inhibitor

Since entinostat activates HIV-1 production in infected cells and has the possibility of causing secondary infection, a combination experiment with an HIV-1 protease inhibitor having a different action site from that of an HDAC inhibitor and acting on the later process of HIV-1 replication to suppress the replication of HIV-1 was performed according to the experimental procedure shown in FIG. 1.

Healthy donor-derived peripheral blood mononuclear cells were infected with HIV-1 strain III$_B$ in vitro to prepare an HIV-1 chronically infected cell model derived from human peripheral blood mononuclear cells, and a combination effect of an HIV-1 protease inhibitor (NFV or SQV) and an HDAC inhibitor (entinostat or vorinostat) was examined.

After HIV-1 infection or pseudo-infection (=mock-infection), the cells were cultured for 7 days and treated with various concentrations of each HIV-1 protease inhibitor for 3 days. For 3 days thereafter, treatment was carried out using combinations of each HIV-1 protease inhibitor having the same concentration and each HDAC inhibitor. The cell viability in each sample was measured by a dye method, and the amount of HIV-1 produced, by an ELISA method (HIV-1 p24 Antigen ELISA).

Figure 2:
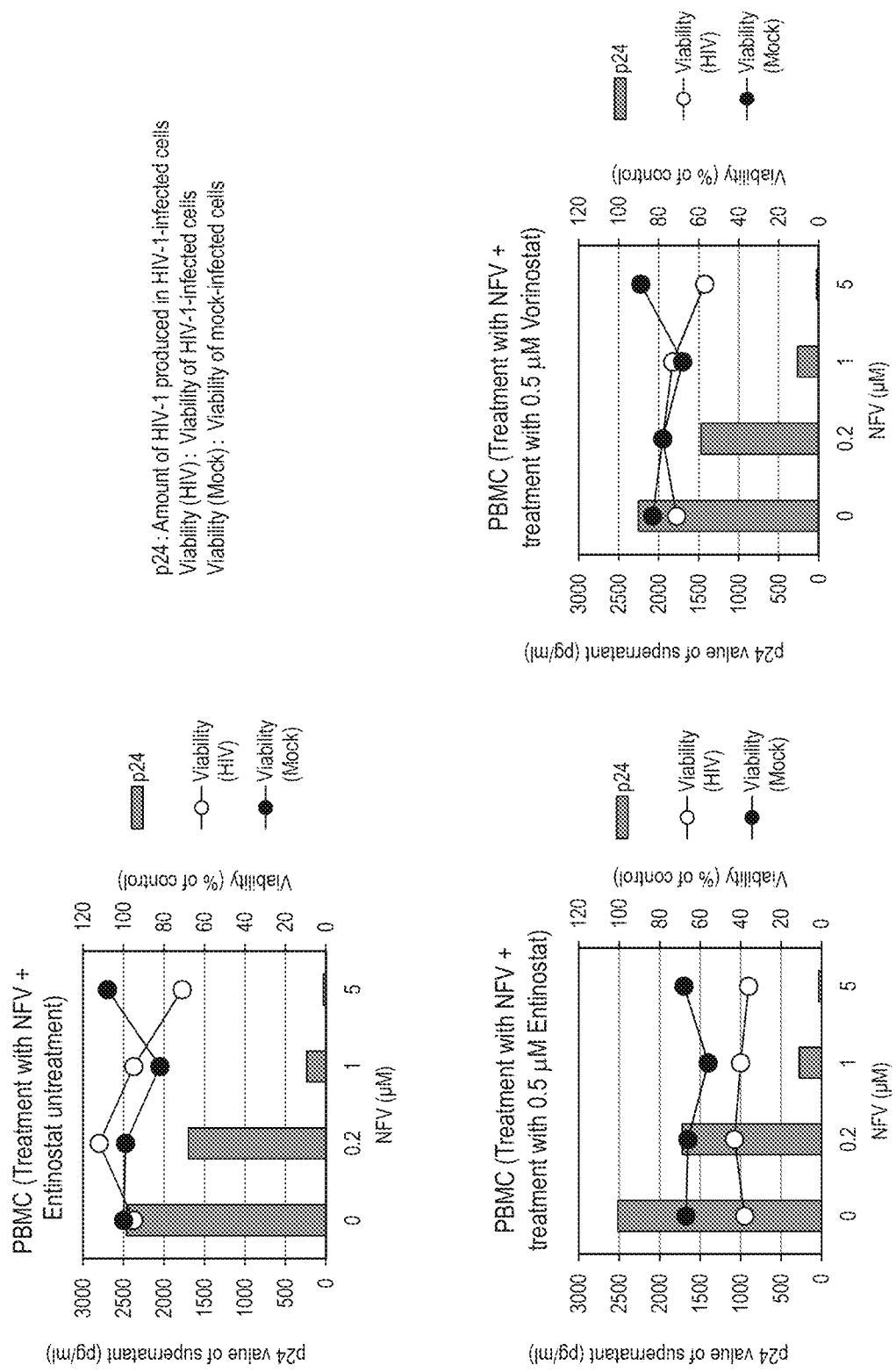
FIG. 2 is a series of graphs showing the action of entinostat or vorinostat in HIV-1-infected ("HIV") and -uninfected ("Mock") human peripheral blood mononuclear cells (PBMC) treated with each concentration of nelfinavir (NFV).
Figure 3:
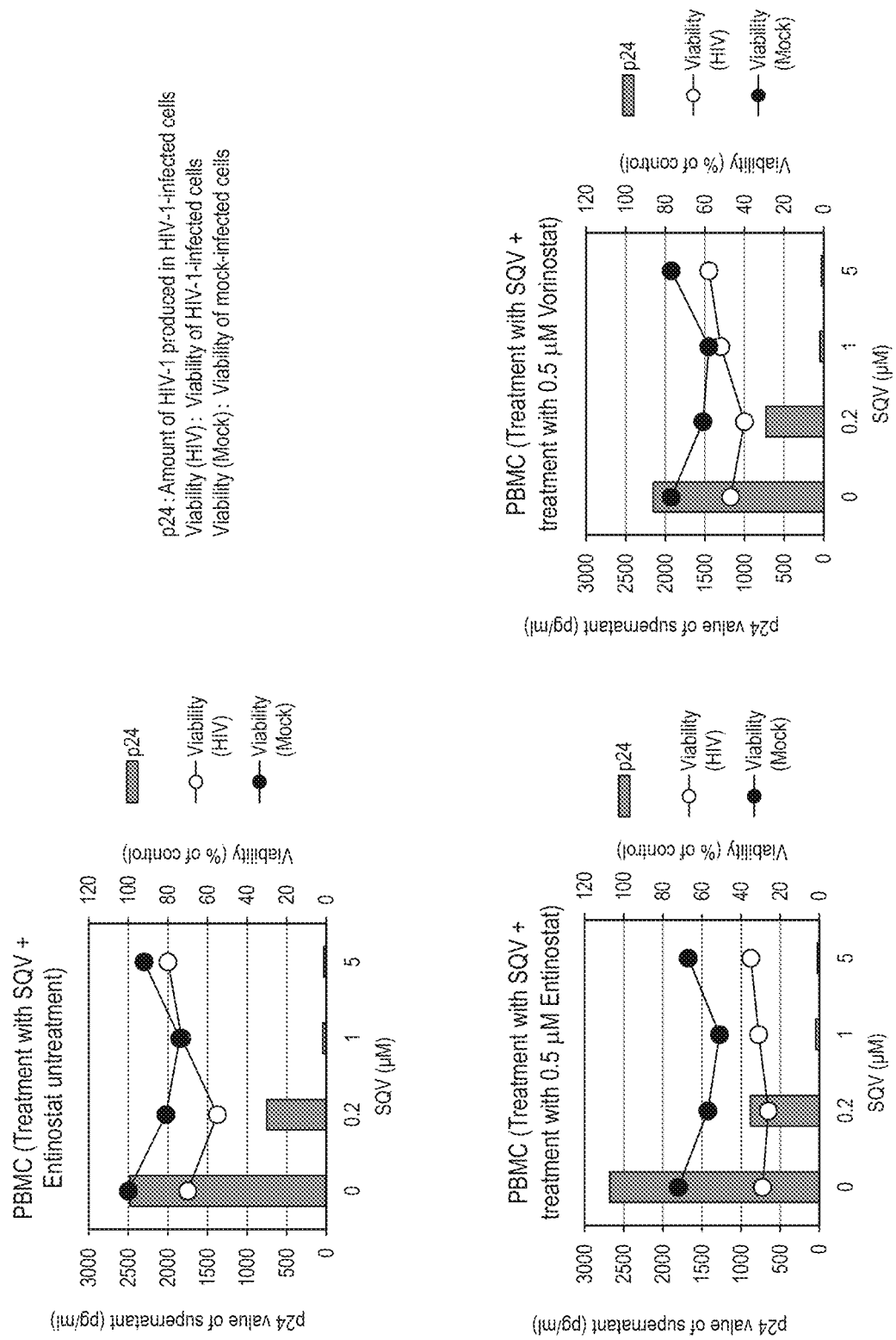
FIG. 3 is a series of graphs showing the action of entinostat or vorinostat in HIV-1-infected ("HIV") and -uninfected ("Mock") human peripheral blood mononuclear cells (PBMC) treated with each concentration of saquinavir (SQV).
Figure 4:
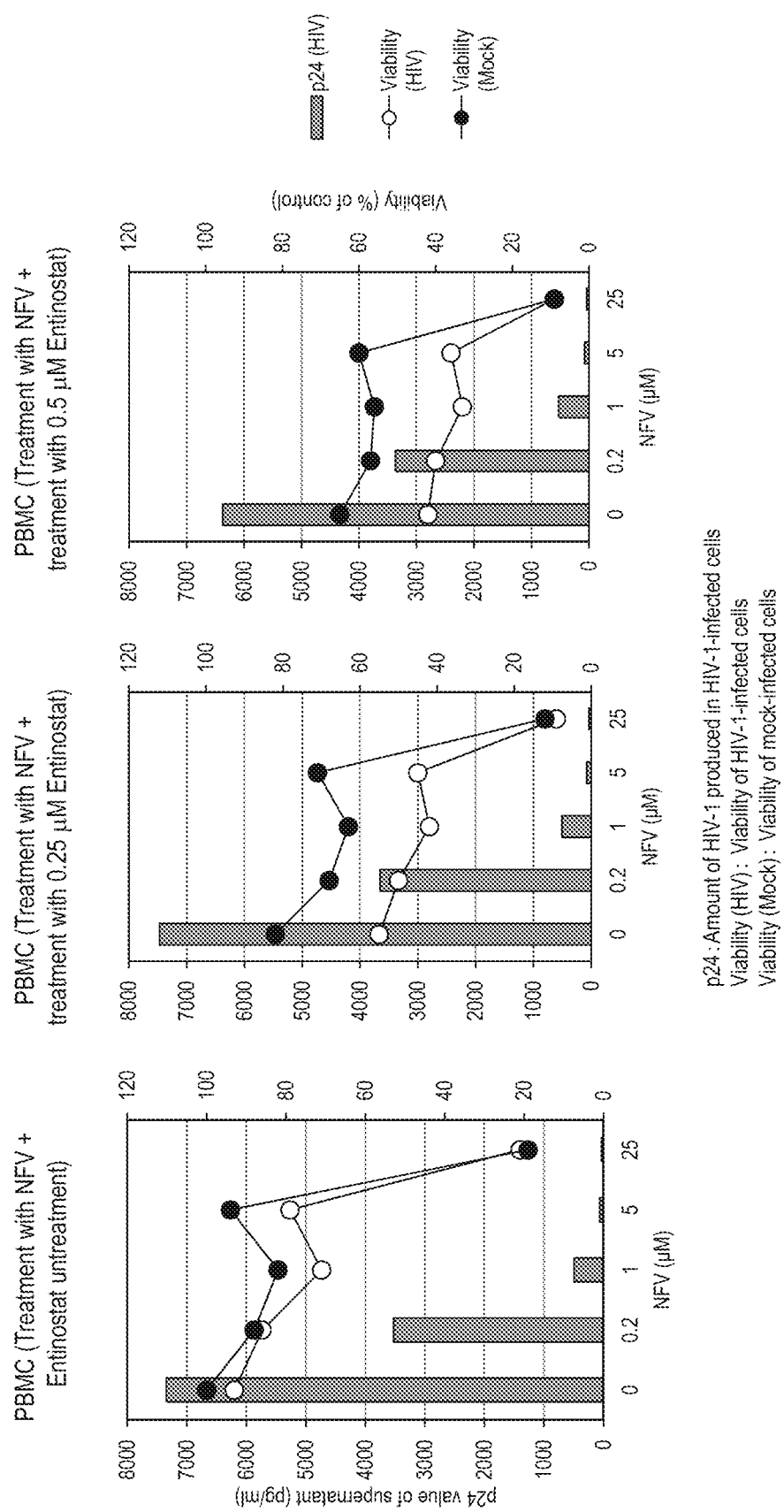
FIG. 4 is a series of graphs showing the action of each concentration of entinostat in HIV-1-infected ("HIV") and -uninfected ("Mock") human peripheral blood mononuclear cells (PBMC) treated with each concentration of nelfinavir (NFV).

The results are shown in FIGS. 2 to 4.

Both NFV and SQV as HIV-1 protease inhibitors concentration-dependently suppressed HIV-1 production in the presence of entinostat of 0.5 µM; however, they did not affect the cell death-inducing effect specific for HIV-1-infected cells due to entinostat.

From these results, it was probable that the combined use of entinostat and an HIV-1 protease inhibitor had the possibility of completely curing HIV-1 infection by decreasing the number of HIV-1-infected cells while suppressing secondary infection due to HIV-1 production activation by entinostat.

Example 3 Combination Effect of HIV-1 Protease Inhibitor and HDAC Inhibitor

In Example 2, it was confirmed that the combined use of an HIV-1 protease inhibitor and an HDAC inhibitor after pretreatment with the HIV-1 protease inhibitor was capable of inducing cell death in infected cells while suppressing HIV-1 production.

Figure 5:
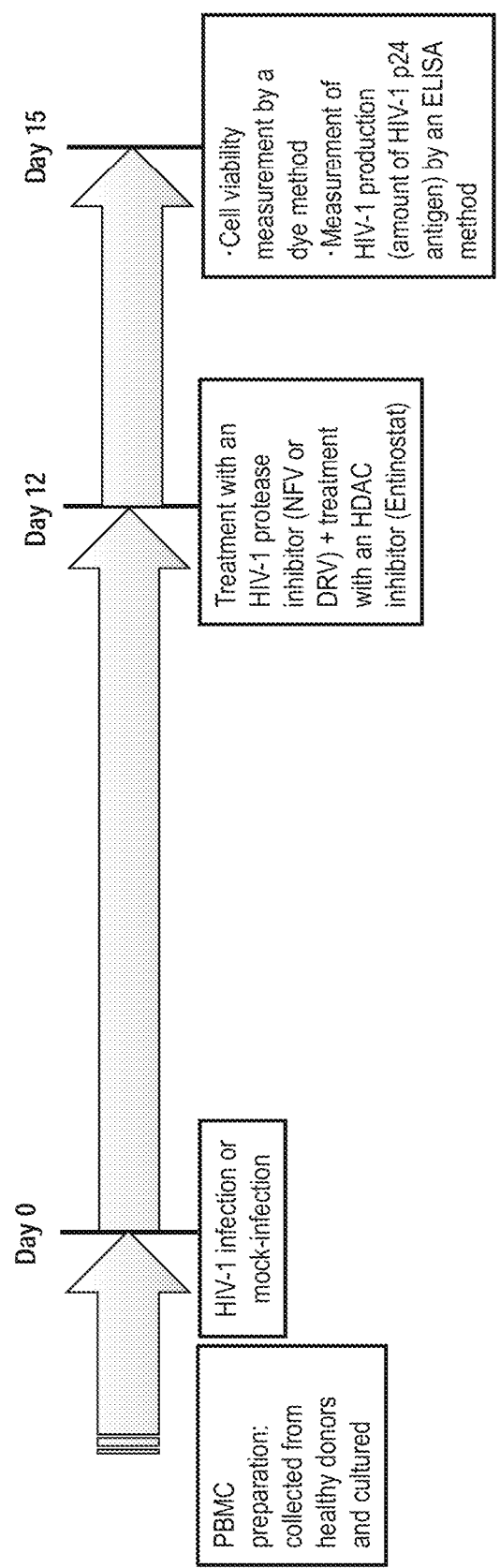
FIG. 5 is a diagram showing the experimental procedure adopted in Example 3.

In this Example, using nelfinavir (NFV) or darunavir (DRV) as an HIV-1 protease inhibitor, a combination experiment with entinostat was conducted according to the experimental procedure shown in FIG. 5 for whether only the simultaneous administration of an HIV-1 protease inhibitor and an HDAC inhibitor provided the same effect.

Healthy donor-derived peripheral blood mononuclear cells were infected with HIV-1 strain III$_B$ in vitro to prepare an HIV-1 chronically infected cell model derived from human peripheral blood mononuclear cells, and a combination effect of an HIV-1 protease inhibitor (NFV or DRV) and an HDAC inhibitor (entinostat) was examined.

After HIV-1 infection or pseudo-infection (=mock-infection), culture was performed for 11 days, and for 3 days from day 12, the combined administration of each HIV-1 protease inhibitor having various concentrations and the HDAC inhibitor was carried out. The cell viability in each sample was measured by a dye method, and the amount of HIV-1 produced, by an ELISA method (HIV-1 p24 Antigen ELISA).

Figure 6:
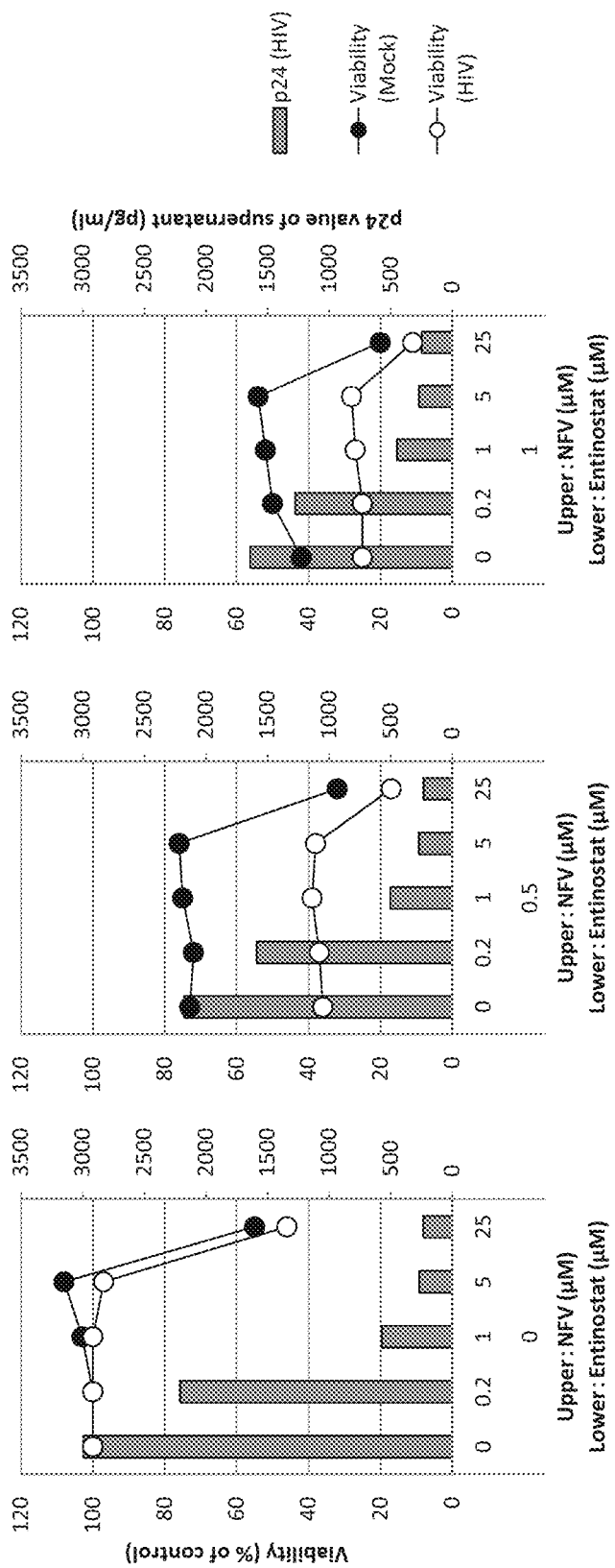
FIG. 6 is a series of graphs showing the results of the combined administration of nelfinavir (NFV) and entinostat in HIV-1-infected ("HIV") and -uninfected ("Mock") human peripheral blood mononuclear cells, performed without pretreatment with a protease inhibitor.
Figure 7:
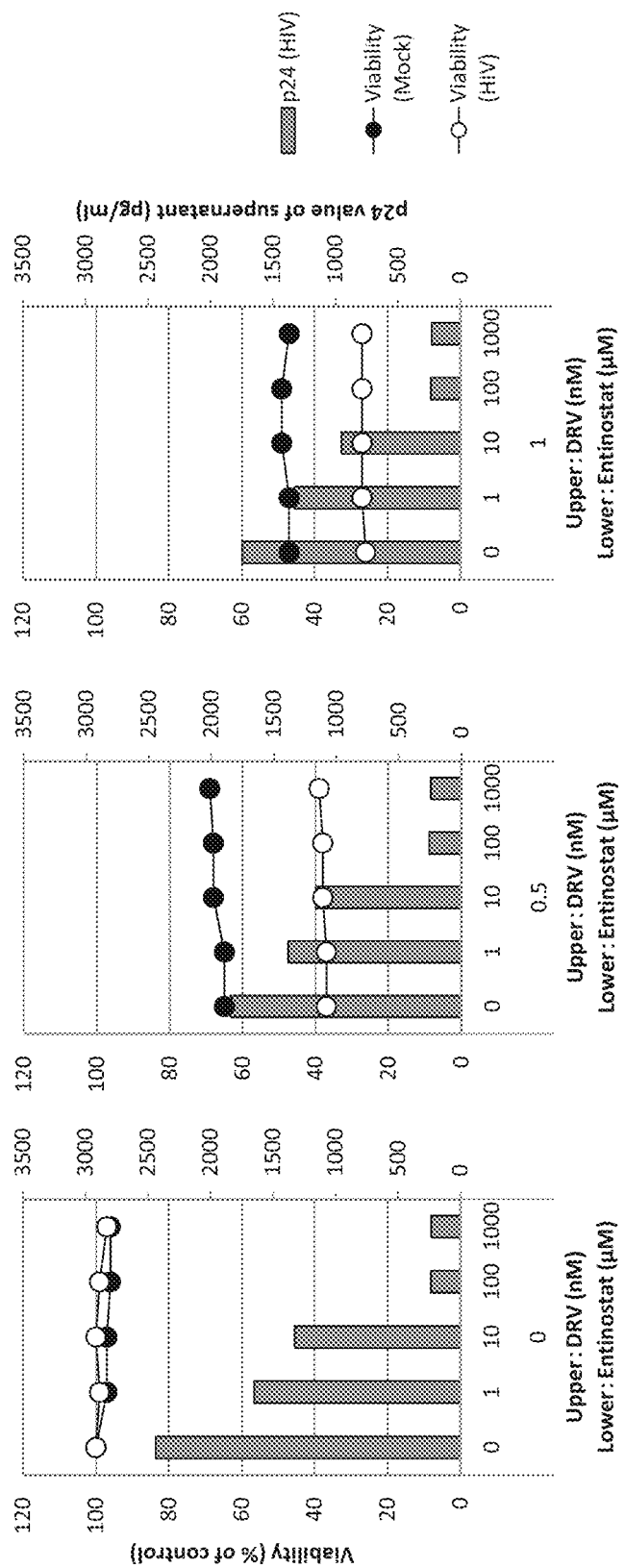
FIG. 7 is a series of graphs showing the results of the combined administration of darunavir (DRV) and entinostat in HIV-1-infected ("HIV") and -uninfected ("Mock") human peripheral blood mononuclear cells, performed without pretreatment with a protease inhibitor.

The results are shown in FIGS. 6 and 7.

In an HIV-1 chronically infected cell model using human peripheral blood mononuclear cells in vitro, it was demonstrated that entinostat was capable of inducing cell death in the infected cells while suppressing HIV-1 production by simultaneous administration of nelfinavir or darunavir as an HIV-1 protease inhibitor.

Particularly, darunavir was not toxic to mock-infected cells up to 1 µM, and further strongly suppressed an increase in HIV-1 production due to entinostat at 100 nM or more completely without affecting the HIV-1-infected cell-specific cell death-inducing effect of entinostat. From these results, it was probable that particularly the combined administration of darunavir and entinostat had the possibility of completely curing HIV-1 infection by efficiently and safely decreasing the number of HIV-1-infected cells while preventing secondary infection due to entinostat.

Figure 8:
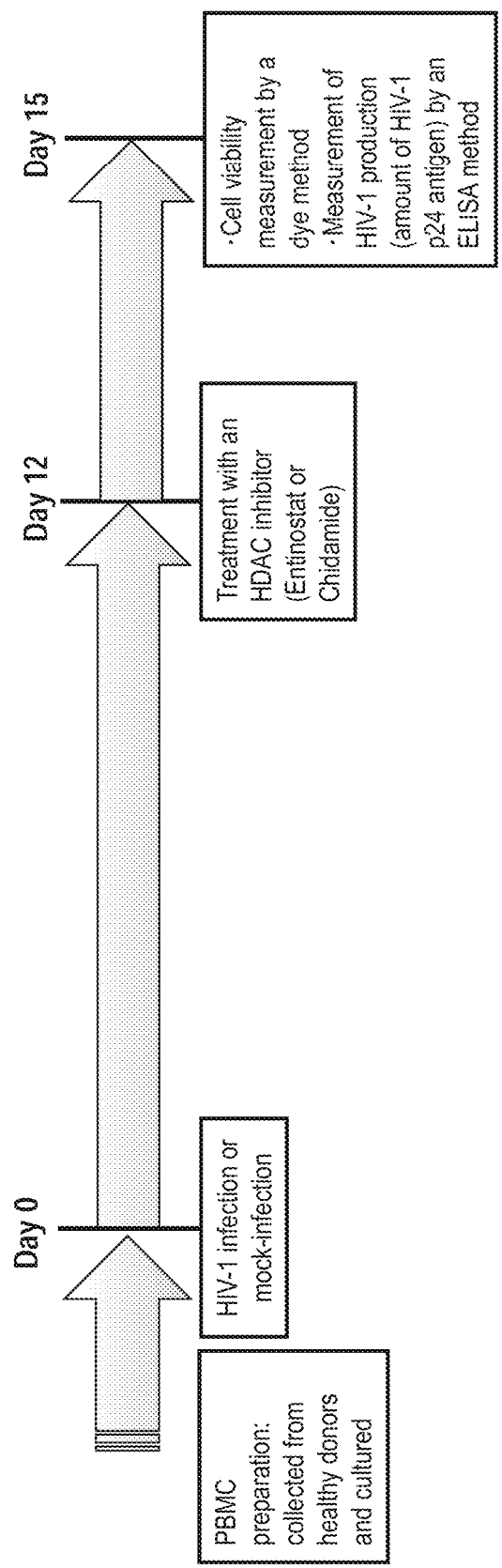
FIG. 8 is a diagram showing the experimental procedure adopted in Example 4.

Example 4 Cell Death-Inducing Effect Specific for HIV-1-Infected Cell Due to Entinostat Derivative, Chidamide The cell death-inducing effect specific for HIV-1-infected cells due to entinostat derivative, chidamide was examined according to the experimental procedure shown in FIG. 8.

Healthy donor-derived peripheral blood mononuclear cells were infected with HIV-1 strain III$_B$ in vitro to prepare an HIV-1 chronically infected cell model derived from human peripheral blood mononuclear cells, which was then exposed to each of HDAC inhibitors (entinostat and chidamide).

After HIV-1 infection or pseudo-infection (=mock-infection), the cells were cultured for 11 days and treated with various concentrations of each HDAC inhibitor. The cell viability in each sample was measured by a dye method, and the amount of HIV-1 produced, by an ELISA method (HIV-1 p24 Antigen ELISA).

Figure 9:
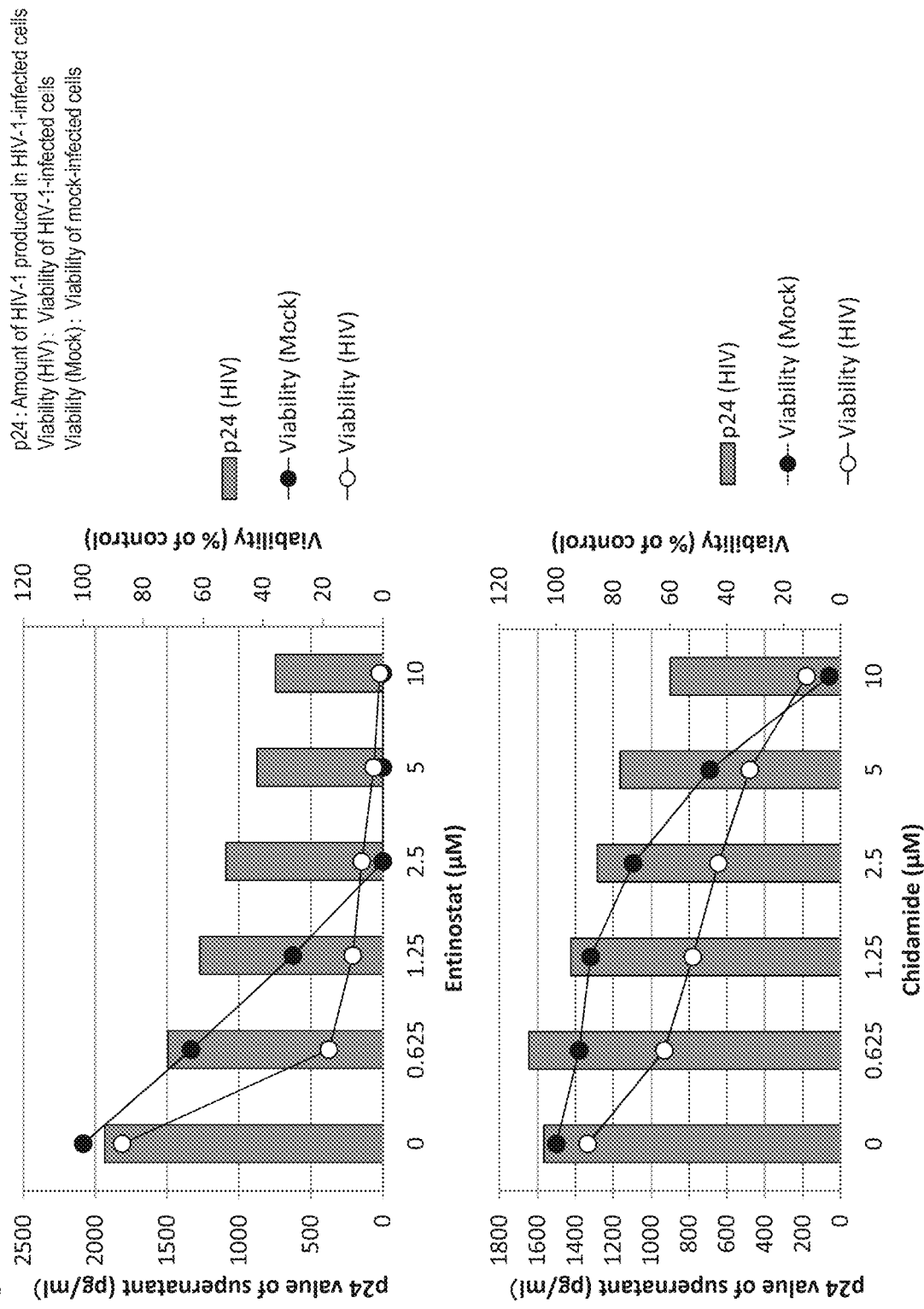
FIG. 9 is a pair of graphs showing the results of treatment with entinostat or chidamide in HIV-1-infected ("HIV") and -uninfected ("Mock") human peripheral blood mononuclear cells.

The results are shown in FIG. 9.

Like entinostat, chidamide had a cell death-inducing effect specific for HIV-1-infected cells. Chidamide was less toxic to mock-infected cells than entinostat; however, it also had a weaker cell death-inducing effect specific for HIV-1-infected cells.

Other derivatives in which $Ar^1$ or $Ar^2$ in the formula (I) was different from that in entinostat or chidamide, for example, derivatives in which $Ar^2$ is a phenyl group having no amino group at 2-position, had a lower cell death-inducing effect specific for HIV-1-infected cells.

Example 5 Cell Death-Inducing Effect Specific for HIV-1-Infected Cell (CD4T)

Cells which are mainly infected with HIV-1 among human peripheral blood nuclear cells are CD4-positive T lymphocytes (CD4T).

In this Example, the action of various HDAC inhibitors on HIV-1-infected CD4T was analyzed using CD4T purified from human peripheral blood mononuclear cells.

Healthy donor-derived CD4T was infected with HIV-1 strain III$_B$ in vitro to prepare a CD4T-derived HIV-1 chronically infected cell model, which was then exposed to each of HDAC inhibitors (entinostat, chidamide, and vorinostat (SAHA)).

Figure 10:
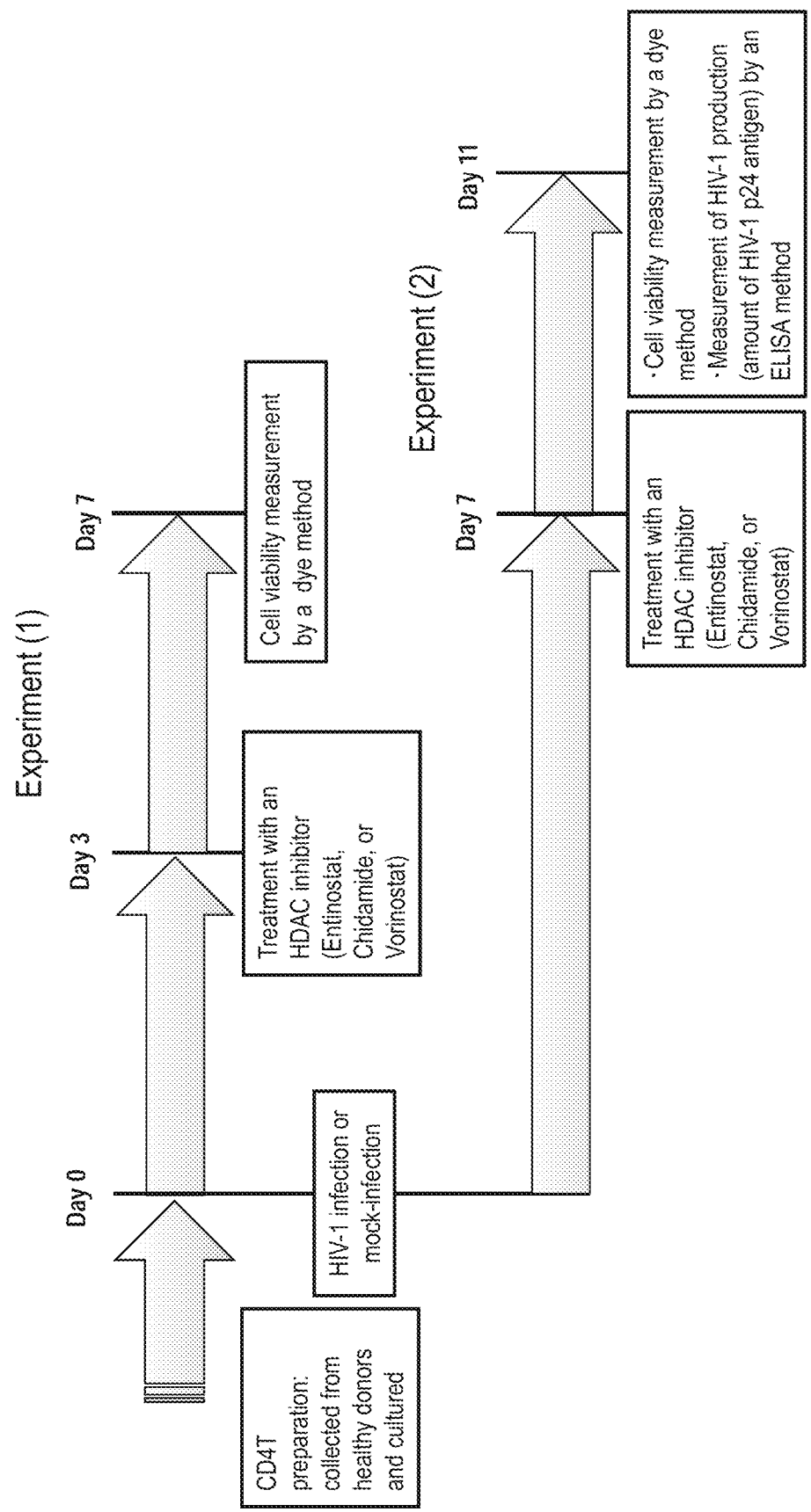
FIG. 10 is a diagram showing the experimental procedure adopted in Example 5.

After HIV-1 infection or pseudo-infection (=mock-infection), the cells were treated with various concentrations of each HDAC inhibitor for 4 days from day 3 in experiment (1) and for 4 days from day 7 in experiment (2). The viability in each sample was measured by a dye method, and the amount of HIV-1 produced, by an ELISA method (HIV-1 p24 Antigen ELISA). The experimental procedure is shown in FIG. 10.

Figure 11:
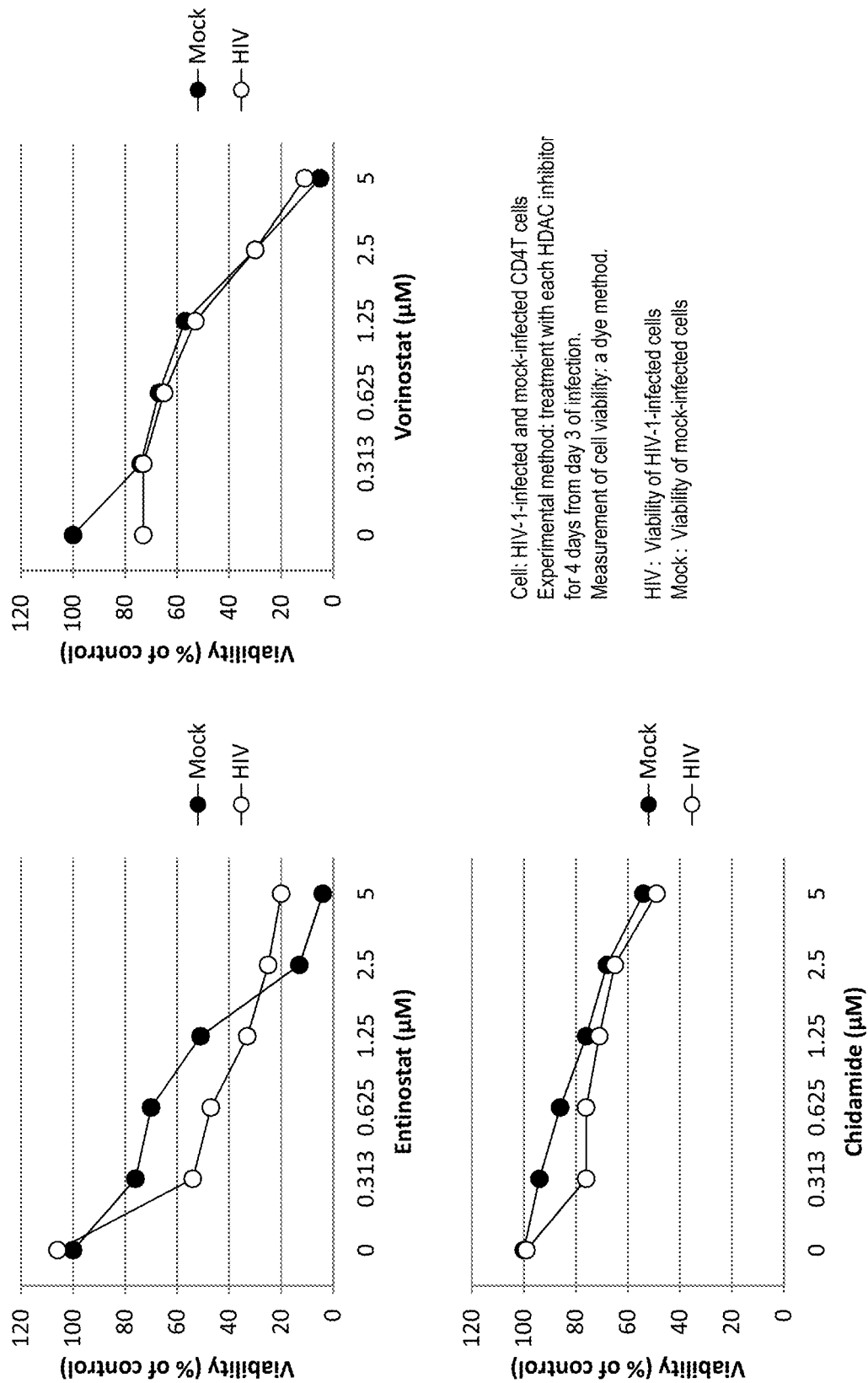
FIG. 11 is a series of graphs showing the results of experiment (1) of Example 5.
Figure 12:
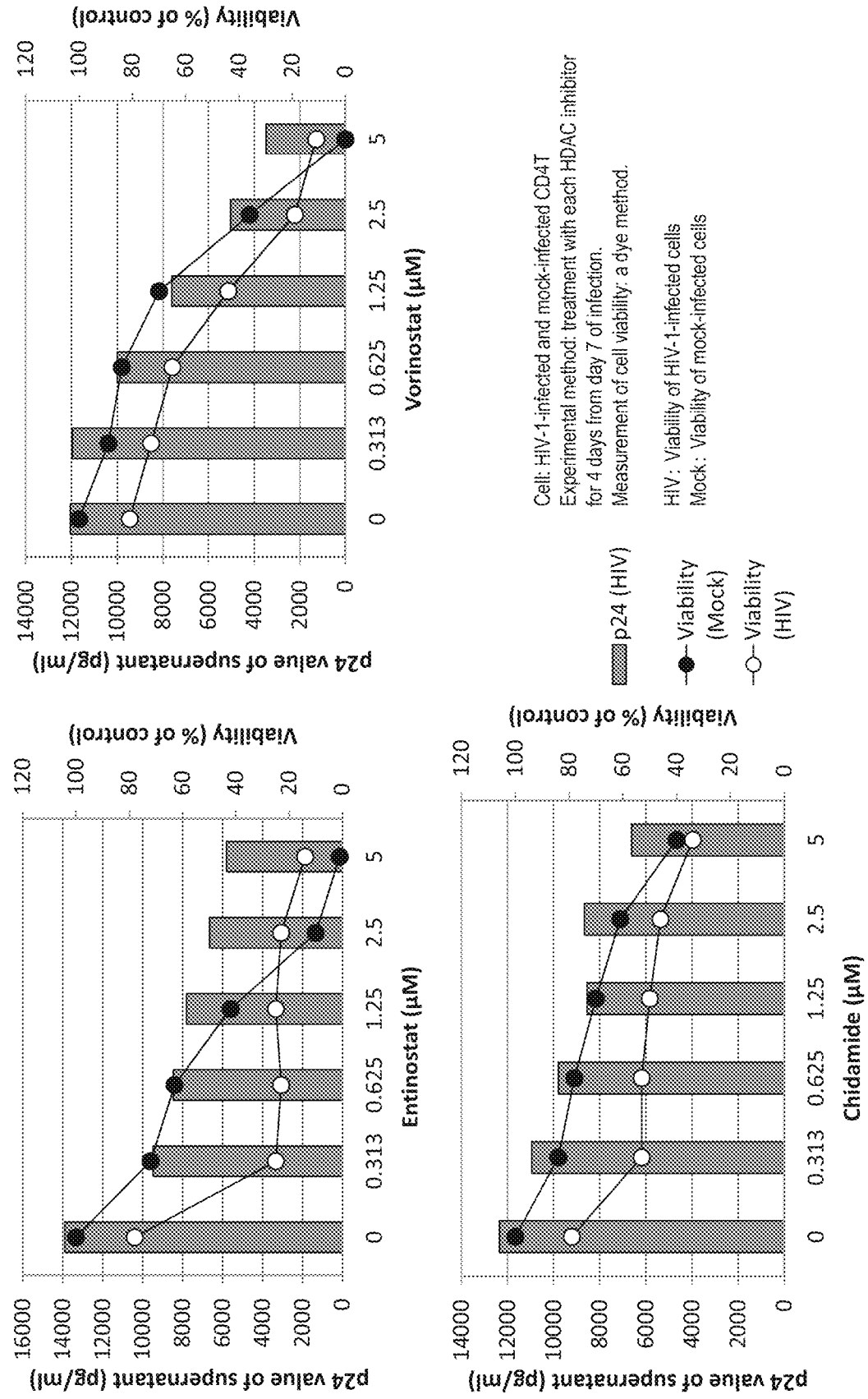
FIG. 12 is a series of graphs showing the results of experiment (2) of Example 5.

The results of experiment (1) are shown in FIG. 11, and the results of experiment (2), in FIG. 12.

Similar to the results from peripheral blood mononuclear cells, entinostat and chidamide also had a cell death-inducing effect specific for HIV-1-infected cells in CD4T. Their effects were observed from as early as day 3 to day 7 after HIV-1 infection.

Chidamide was less toxic to mock-infected cells compared to entinostat; however, it also had a weaker cell death-inducing effect against infected cells.

In contrast, vorinostat (SAHA) also had no cell death-inducing effect specific for HIV-1-infected cells in CD4T.

The above results demonstrated that entinostat and chidamide exerted a cell death-inducing effect specific for HV-1-infected cells from early after infection in CD4T. This probably had the possibility of being associated with the efficient infection of HIV-1 in CD4T compared to that in peripheral blood mononuclear cells Example 6 Combined Use of HIV-1 Protease Inhibitor, HIV-1 Reverse Transcriptase Inhibitor, or HIV-1 Integrase Inhibitor and HDAC Inhibitor It was demonstrated that entinostat and chidamide (an entinostat derivative) as HDAC inhibitors induced infected cell-specific cell death in a HIV-1 chronically infected cell model using human peripheral blood mononuclear cells in vitro.

It was also confirmed that combined use with an HIV-1 protease inhibitor, such as darunavir, could induce cell death in infected cells while suppressing HIV-1 production activated by entinostat.

Figure 13:
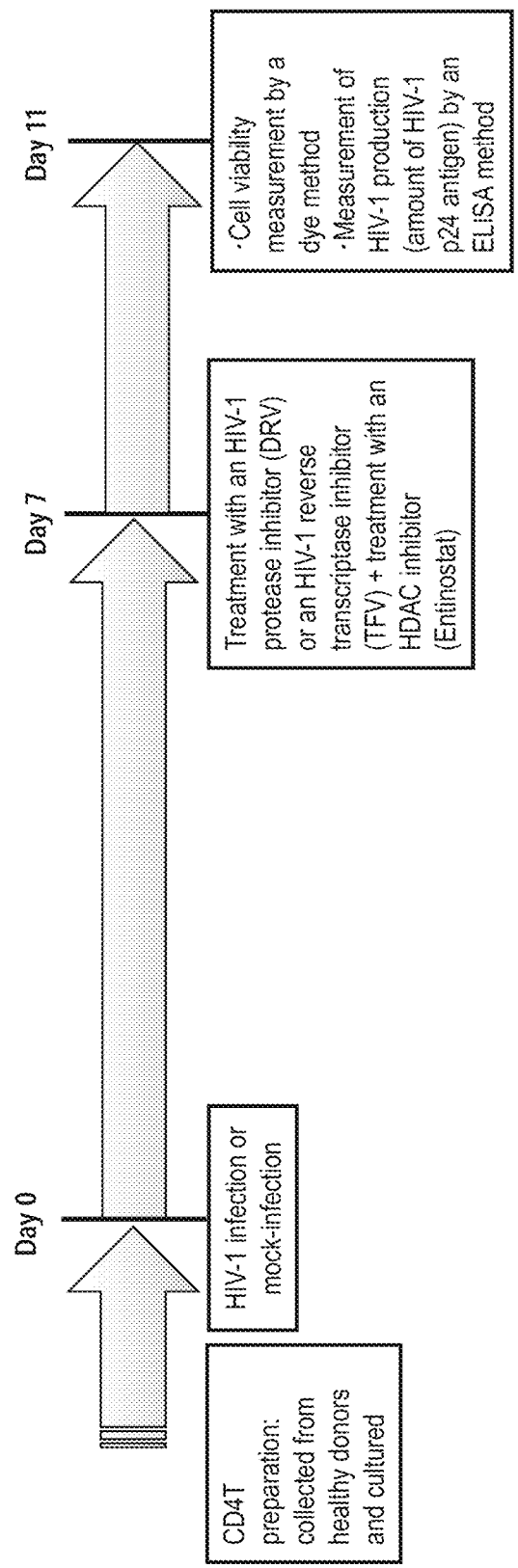
FIG. 13 is a diagram showing the experimental procedure adopted in Example 6.

In this Example, it was examined whether combined use with an HIV-1 reverse transcriptase inhibitor provided the same effect, by conducting a combination experiment with entinostat according to the experimental procedure shown in FIG. 13 using tenofovir (TFV) as one of the clinically most used HIV-1 reverse transcriptase inhibitors.

Figure 14:
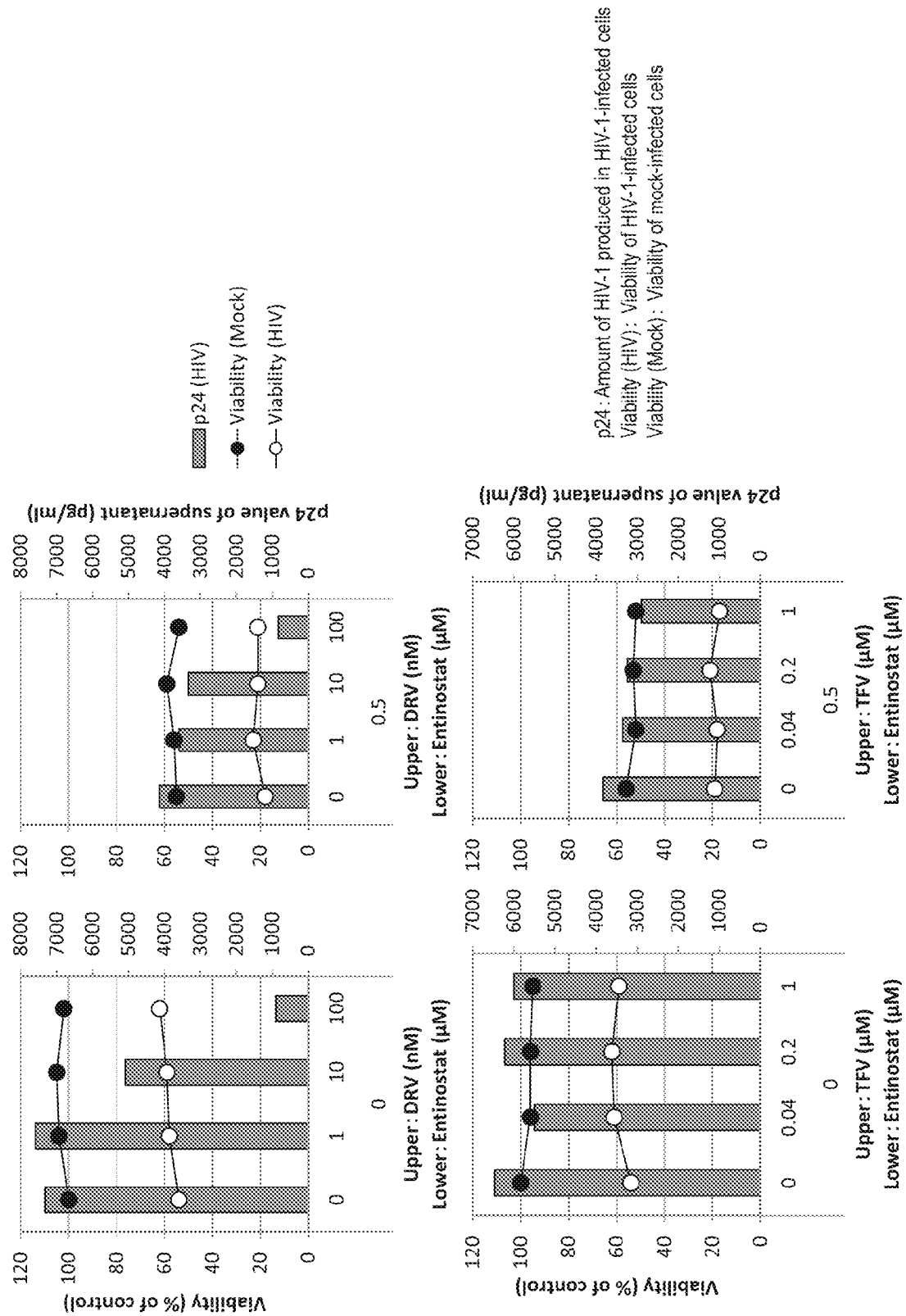
FIG. 14 is a series of graphs showing the results of Example 6.

The results are shown in FIG. 14.

In an HIV-1 chronically infected cell model using human CD4-positive T lymphocytes (CD4T) in vitro, it was demonstrated that darunavir (DRV) as an HIV-1 protease inhibitor having a concentration of 100 nM was administered simultaneously with entinostat to be capable of specifically inducing cell death in the infected cells while strongly suppressing the activation of HIV-1 production by entinostat.

However, tenofovir (TFV) did not affect a cell death-inducing effect specific for HIV-1-infected cells due to entinostat, but did not suppress HIV-1 production even in a concentration of 1 µM irrespective of the presence or absence of entinostat. This suggests that (1) HIV-1-infected CD4T was already in a state of chronically infected cells at day 7 after infection and (2) tenofovir as an HIV-1 reverse transcriptase inhibitor could not suppress HIV-1 production since entinostat activated the transcription of HIV-1 gene integrated in genomic gene.

Figure 15:
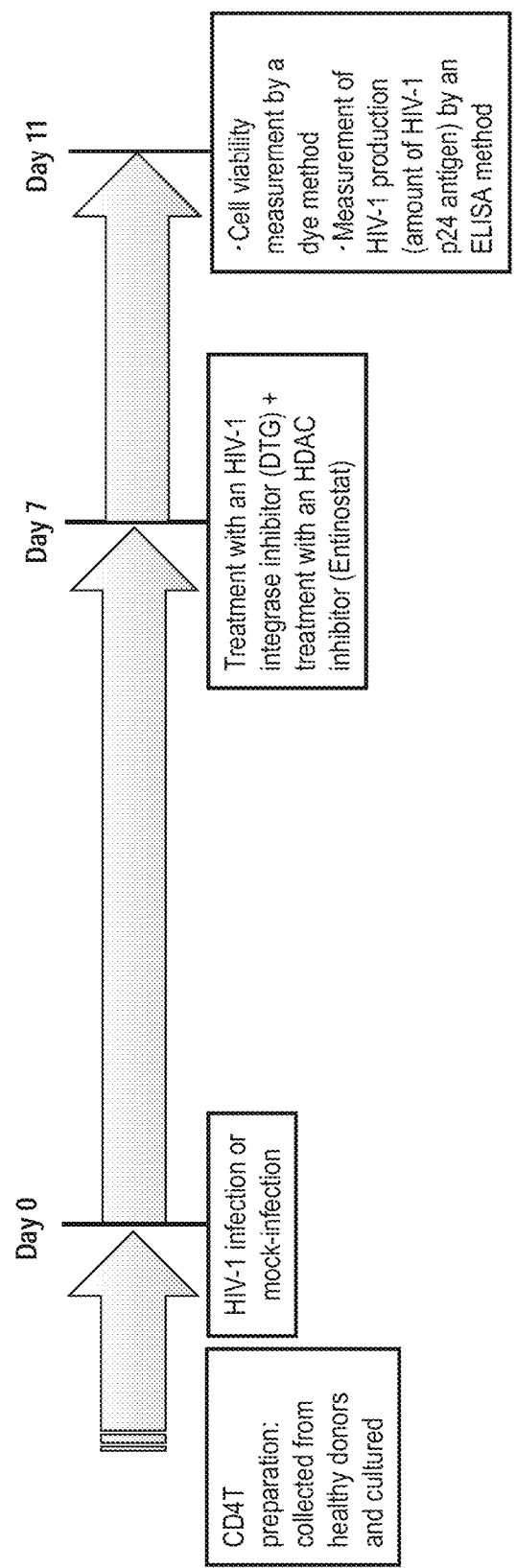
FIG. 15 is a diagram showing the experimental procedure adopted in Example 6 (using dolutegravir (DTG)).

Then, it was examined whether combined use with an HIV-1 integrase inhibitor provided the same effect by conducting a combination experiment with entinostat according to the experimental procedure shown in FIG. 15 using dolutegravir (DTG) as one of the clinically most used HIV-1 integrase inhibitors.

Figure 16:
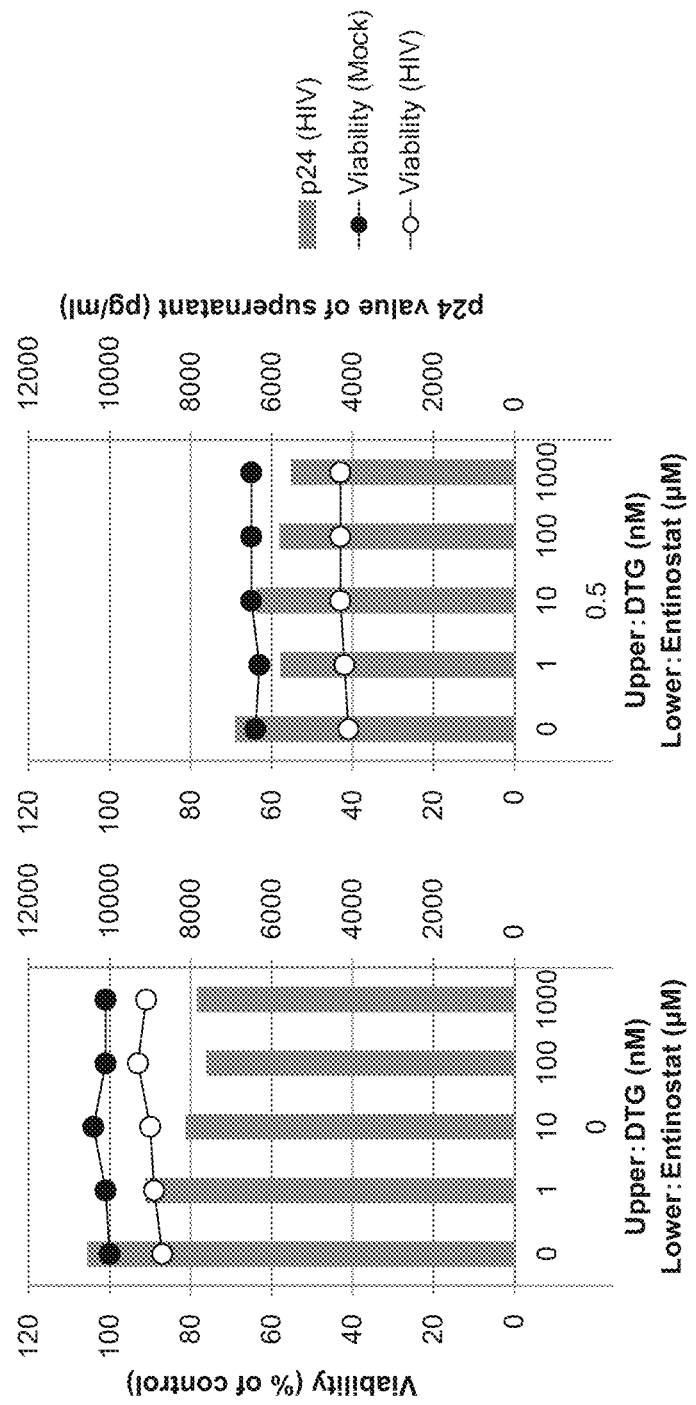
FIG. 16 is a pair of graphs showing the results obtained when dolutegravir (DTG) was used in Example 6.

The results are shown in FIG. 16.

In an HIV-1 chronically infected cell model using human CD4-positive T lymphocytes (CD4T) in vitro, dolutegravir (DTG) as an HIV-1 integrase inhibitor hardly had an anti-HIV-1 effect in the absence of entinostat. The inhibitor did not affect a cell death-inducing effect specific for HIV-1-infected cells due to entinostat in the presence of entinostat, but did not suppress HIV-1 production even in a concentration of 1 M. This suggests that (1) HIV-1-infected CD4T was already almost in a state of chronically infected cells at day 7 after infection and (2) dolutegravir (DTG) as an HIV-1 integrase inhibitor could not suppress HIV-1 production since entinostat activated the transcription of HIV-1 gene integrated in genomic gene.

From these results, it was probable that decreasing the number of HIV-1-infected cells while preventing secondary infection due to entinostat required combined use with an anti-HIV-1 drug capable of suppressing HIV-1 production from chronically infected cells, such as an HIV-1 protease inhibitor.

In addition, an HIV-1 reverse transcriptase inhibitor and an HIV-1 integrase inhibitor cannot suppress HIV-1 production activated by entinostat in chronically infected cells, but it is probable that, in the clinical setting, the combined use of entinostat or chidamide (entinostat derivative) as an HDAC inhibitor with an HIV-1 protease inhibitor, such as darunavir, and further with an HIV-1 reverse transcriptase inhibitor or an HIV-1 integrase inhibitor can more strongly prevent secondary infection (these agents act in other uninfected cells).

Example 7 Analysis of Cell Death Induction Mechanism

Cells which are mainly infected with HIV-1 among human peripheral blood nuclear cells are CD4-positive T lymphocytes (CD4T).

In this Example, the cell death induction mechanism was analyzed using CD4T purified from human peripheral blood mononuclear cells.

Healthy person-derived CD4T was infected with HIV-1 strain $III_B$ in vitro to prepare a CD4T-derived HIV-1 chronically infected cell model, which was then exposed to an HDAC inhibitor (entinostat).

Figure 17:
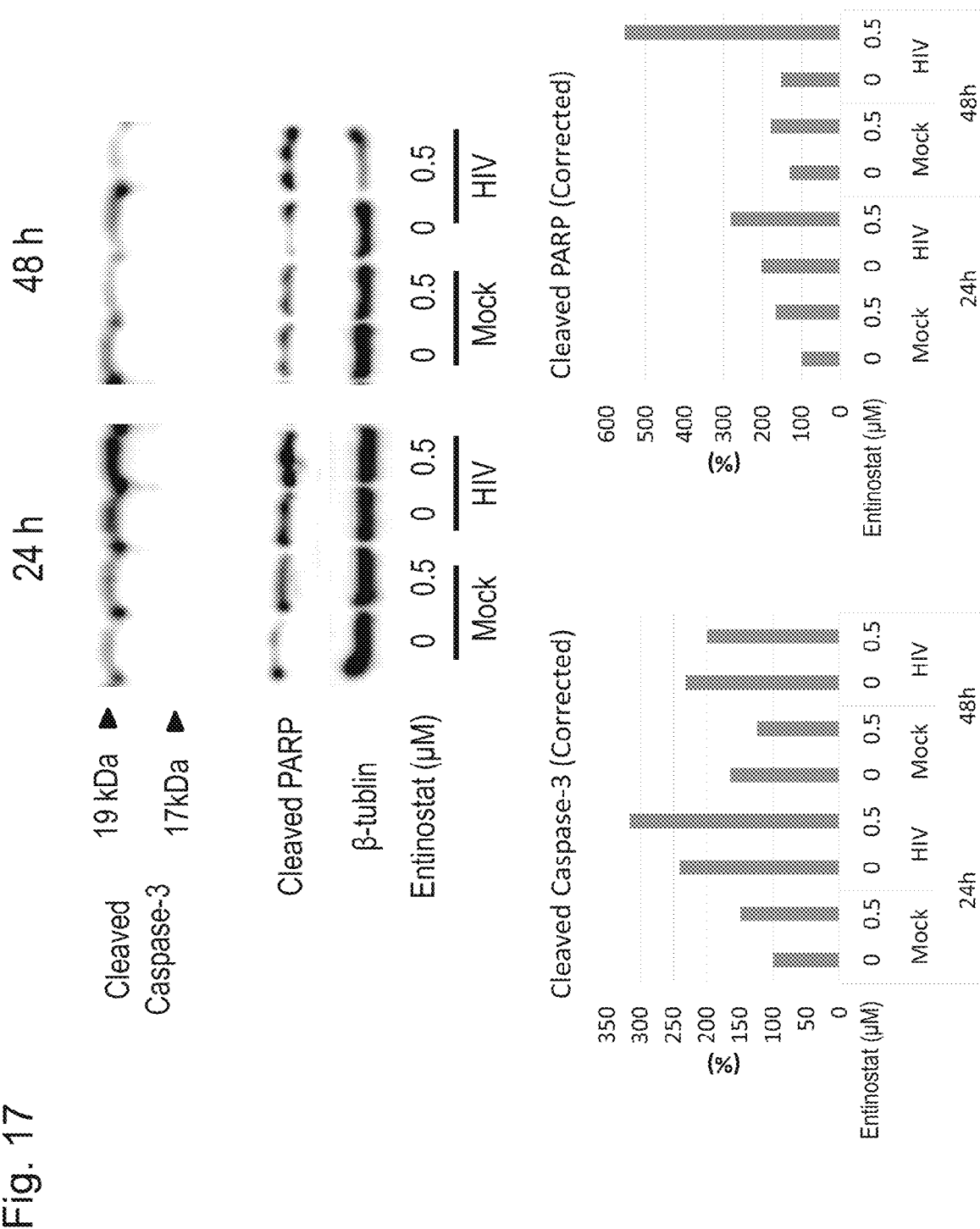
FIG. 17 is a series of drawings showing the results of treatment with entinostat in HIV-1-infected ("HIV") and -uninfected ("Mock") CD4-positive T lymphocytes (CD4T).

After HIV-1 infection or pseudo-infection (=mock-infection), the cells were treated with an HDAC inhibitor (entinostat) of 0.5 µM for 24 or 48 hours from day 7. The extracted protein was analyzed by a Western blot method. The results are shown in FIG. 17.

The expression of each of Cleaved caspase-3 and Cleaved PARP was corrected with the expression of β-tublin as an internal control to make a graph.

For treatment with entinostat of 0.5 µM for 24 hours, the increase in an activated form of caspase-3 (cleaved caspase-3) as a protease capable of inducing apoptosis in pseudo-infected CD4T (Mock) and HIV-1-infected CD4T (HIV) was observed; its increase was more marked in the HIV-1-infected CD4T (HIV). For treatment with entinostat of 0.5 µM for 48 hours, the increase in an activated form of caspase-3 due to treatment with entinostat was not observed in pseudo-infected CD4T and HIV-1-infected CD4T, which was probably because the decomposition of the activated form of caspase-3 due to cell death had proceeded.

The expression of PARP cleaved by an activated caspase group (cleaved PARP) is also sustained during the late stage of apoptosis. For treatment of pseudo-infected CD4T and HIV-1-infected CD4T with entinostat of 0.5 μM for 24 hours, the increase in the cleaved PARP was observed. In addition, the expression of PARP was markedly increased in HIV-1-infected CD4T treated with entinostat for 48 hours.

From these results, it was probable that entinostat specifically induced cell death in HIV-1-infected CD4T via apoptosis.

All publications, patents, and patent applications cited in this application are intended to be incorporated herein by reference in their entirety.

The invention claimed is:

1. A method for killing HIV-1-infected cells comprising administering to a subject in need thereof an effective amount of a compound represented by formula (I):

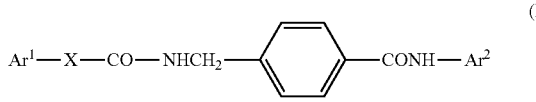

wherein $Ar^1$ and $Ar^2$ are the same or different and represent a substituted or unsubstituted aromatic group, and X represents —$CH_2O$— or —CH=CH—, a salt thereof, or a solvate of these.

2. The method according to claim 1, wherein in the formula (I), $Ar^1$ and $Ar^2$ are the same or different and represent a phenyl group or a pyridyl group, and the phenyl group or the pyridyl group is optionally substituted by one or more substituents selected from an amino group, $C_1$ to $C_6$ alkyl groups, and halogen atoms.

3. The method according to claim 1, wherein in the formula (I), $Ar^1$ represents a pyridyl group and $Ar^2$ represents a phenyl group optionally substituted by one or more substituents selected from an amino group and halogen atoms.

4. The method according to claim 1, wherein the subject is an HIV-1-infected person not suffering from cancer.

5. The method according to claim 1, which further comprises administering an anti-HIV-1 drug.

6. The method according to claim 5, wherein the anti-HIV-1 drug is at least one selected from HIV-1 protease inhibitors.

\* \* \* \* \*

UNITED STATES PATENT AND TRADEMARK OFFICE
CERTIFICATE OF CORRECTION

PATENT NO. : 9,839,645 B2
APPLICATION NO. : 15/651667
DATED : December 12, 2017
INVENTOR(S) : Mika Okamoto Page 1 of 1

It is certified that error appears in the above-identified patent and that said Letters Patent is hereby corrected as shown below:

On the Title Page

On (73), Assignee section, "Kogoshima-Shi, Kagoshima (JP)" should read --Kagoshima-Shi, Kagoshima (JP)--.

Signed and Sealed this
Twenty-sixth Day of February, 2019

Andrei Iancu
*Director of the United States Patent and Trademark Office*